United States Patent [19]

Borror et al.

[11] Patent Number: 4,469,877

[45] Date of Patent: Sep. 4, 1984

[54] PHOTOGRAPHIC PRODUCTS

[75] Inventors: Alan L. Borror, Lexington; Ernest W. Ellis, Carlisle, both of Mass.

[73] Assignee: Polaroid Corporation, Cambridge, Mass.

[21] Appl. No.: 475,222

[22] Filed: Mar. 14, 1983

Related U.S. Application Data

[62] Division of Ser. No. 360,822, Mar. 23, 1982, Pat. No. 4,388,398.

[51] Int. Cl.³ .................. C07D 339/00; C07D 339/08
[52] U.S. Cl. ........................................ 549/21; 546/22; 546/268; 548/119; 548/203; 548/252; 549/5; 549/11
[58] Field of Search ................. 549/5, 11, 21; 546/22, 546/268; 548/119, 203, 252

[56] References Cited

U.S. PATENT DOCUMENTS

| | | | |
|---|---|---|---|
| 3,698,898 | 10/1972 | Grasshoff et al. | 430/219 |
| 3,932,480 | 1/1976 | Grasshoff et al. | 430/455 |
| 3,958,992 | 5/1976 | Greenwald | 430/455 |
| 4,126,459 | 11/1978 | Greenwald | 430/251 |
| 4,348,529 | 9/1982 | Borror et al. | 549/11 |

OTHER PUBLICATIONS

Herz et al., Silver Halide Complexing Agents, Research Disclosure, No. 13405, 6-1975, pp. 6-8.

Primary Examiner—Richard Raymond
Attorney, Agent, or Firm—Sybil A. Campbell

[57] ABSTRACT

This invention relates to photographic products and processes employing silver halide solvent precursors of the formula

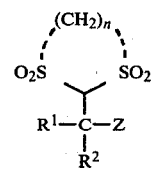

wherein $R^1$ is a monovalent organic radical; $R^2$ is hydrogen or a monovalent organic radical; Z is a moiety that undergoes β-elimination in aqueous alkaline solution and preferably is a moiety that undergoes β-elimination in aqueous alkaline solution to release a photographically useful reagent; and n is an integer 3, 4 or 5.

6 Claims, 2 Drawing Figures

PHOTOGRAPHIC PRODUCTS

This is a division of application Ser. No. 360,822, filed Mar. 23, 1982, now U.S. Pat. No. 4,388,398.

BACKGROUND OF THE INVENTION

1. Field of the Invention

This invention relates to compounds which release a silver halide solvent in the presence of alkali and to photographic products and processes employing said compounds.

2. Description of the Prior Art

In various photographic processes for forming images in either black-and-white or in color, it is often desirable to include one or more of the photographic reagents in the photographic film unit. In many instances, the photographic reagent may be contained initially in either the processing composition or in the film unit, the latter being preferred to reduce the number of ingredients in the processing composition. In other instances, the particular photographic reagent selected may not be sufficiently stable in alkali to provide the requisite shelf life of the processing composition, or it may be incompatible, e.g., reactable with another ingredient in the processing composition. In still other instances, it may be desirable to provide a given reagent at some particular time during the development process which requires positioning of the reagent in a particular layer or layers of the film unit. In all of these instances it is desirable that the reagent initially positioned in the film unit be stable, i.e., substantially inert until it is required during the development process.

One class of compounds which releases a photographic reagent during processing in the presence of alkali is disclosed in U.S. Pat. No. 3,698,898 of J. Michael Grasshoff and Lloyd D. Taylor. These compounds are phenols and naphthols (including protected derivatives thereof) containing a photographic reagent bonded to a nuclear carbon atom through a methylene substituent in a position ortho or para to the hydroxyl group. The photographic reagent released may be an antifoggant, development arrester or restrainer, toning agent, silver halide solvent, etc. U.S. Pat. No. 3,932,480, a continuation-in-part of Ser. No. 230,064 filed Feb. 28, 1972, now abandoned, which, in turn, is a division of aforementioned U.S. Pat. No. 3,698,898 is directed to such compounds which release a thiosulfate silver halide solvent.

Another class of compounds that release a silver halide solvent in alkaline solution during processing is disclosed and claimed in U.S. Pat. No. 4,382,119 issued May 3, 1983, a continuation-in-part of copending U.S. patent application Ser. No. 294,311 of Alan L. Borror and Ernest W. Ellis filed Aug. 19, 1981, now abandoned. These compounds release a silver halide solvent via a Michael addition of hydroxide followed by a retro-aldol reaction and include compounds, such as,

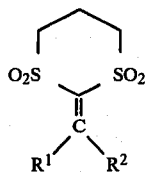

wherein $R^1$ and $R^2$ are groups selected to provide a given release rate at a given alkali concentration.

The present invention is concerned with a new class of compounds that release a silver halide solvent in the presence of alkali.

SUMMARY OF THE INVENTION

It is therefore the primary object of the present invention to provide photographic products and processes employing certain silver halide solvent release compounds.

It is another object of the present invention to provide novel silver halide solvent release compounds.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description taken in connection with the accompanying drawings.

DETAILED DESCRIPTION OF THE INVENTION

Figure 1:
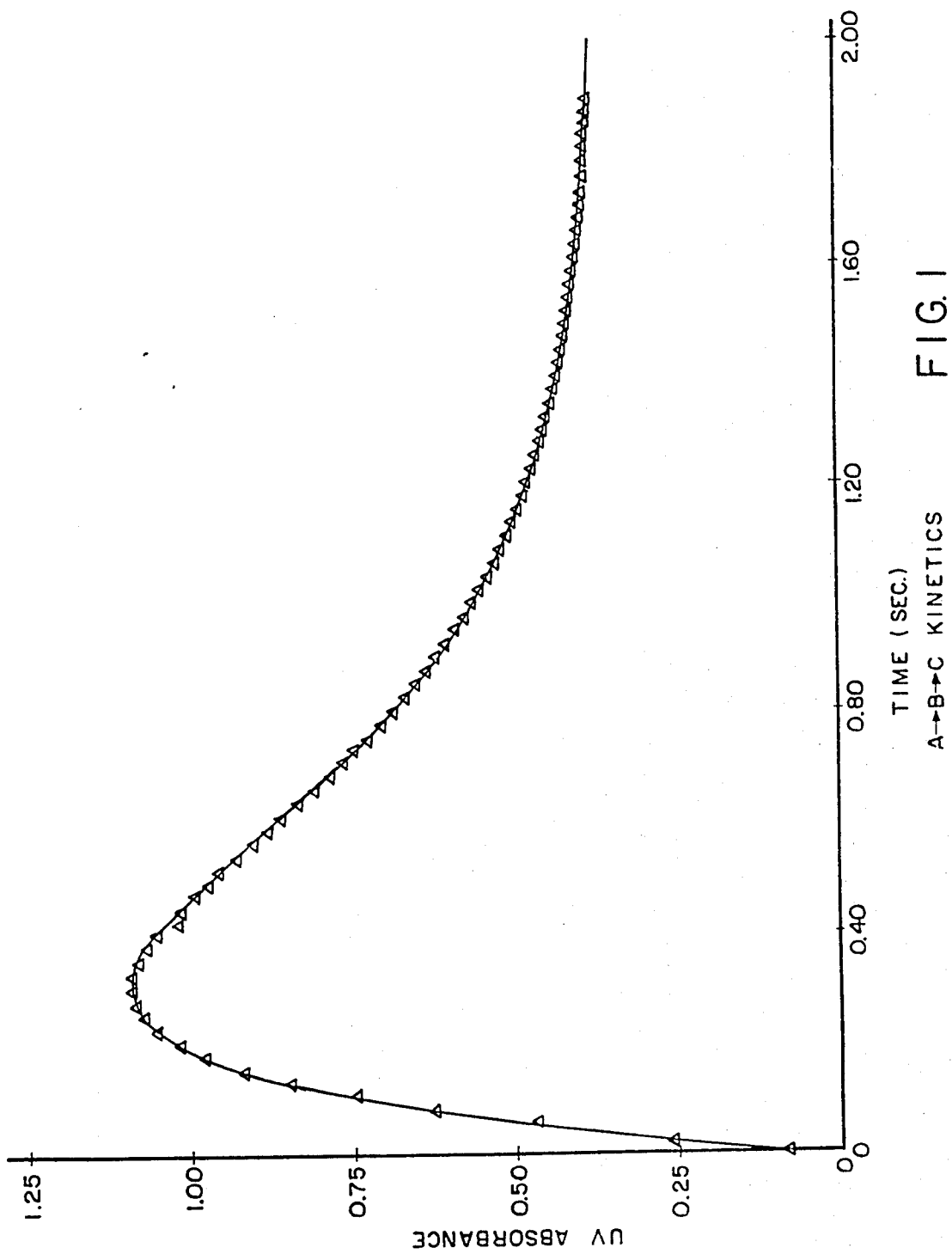
FIG. 1 is a graph showing the A→B→C kinetics of the silver solvent release compound of Example 1 of the present invention obtained by measuring UV absorbance of the compound in alkaline acetonitrile solution at intervals over a time period of 2 seconds.

According to the present invention, photographic silver halide solvents are released from certain compounds in the presence of alkali during photographic processing via a β-elimination reaction followed by a Michael addition of hydroxide and a subsequent retro-aldol reaction. These silver halide solvent release compounds may be represented by the formula

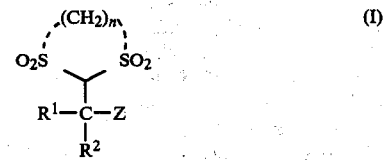

wherein $R^1$ is a monovalent organic radical; $R^2$ is hydrogen or a monovalent organic radical; Z is a moiety that undergoes β-elimination in aqueous alkaline solution and preferably is a moiety that undergoes β-elimination in aqueous alkaline solution to release a photographically useful reagent; and n is an integer 3, 4 or 5. The monovalent organic radicals comprising $R^1$ and $R^2$ typically are alkyl, usually alkyl having 1 to 20 carbon atoms, e.g., methyl, ethyl, isopropyl, isobutyl, hexyl, dodecyl, hexadecyl, etc.; cycloalkyl having up to 8 carbon atoms, e.g., cyclobutyl, cyclopropyl, cyclohexyl, cycloheptyl, etc.; aralkyl, e.g., phenyl-substituted alkyl wherein the alkyl usually has 1 to 20 carbon atoms; alkaryl, e.g., alkyl-substituted phenyl wherein the alkyl usually has 1 to 20 carbon atoms; aryl, substituted and unsubstituted, e.g., phenyl, biphenyl and naphthyl and phenyl substituted in the o-, m- or p-position with an electron-donating group or an electron-withdrawing group; and heterocyclic aryl containing O, N, S and combinations thereof, substituted or unsubstituted, e.g., pyridyl, methylpyridyl, thiazolyl, tetrazolyl, pyranyl, furyl and thienyl including the various isomers of these groups. It will be appreciated that the moieties selected for $R^1$, $R^2$ and Z may be substituted with a solubilizing group, such as, carboxy, hydroxy, or sulfo or other group as may be appropriate for a given photographic system.

By electron-donating group is intended "a group with a negative sigma value as defined by Hammett's Equation", and by electron-withdrawing group is intended "a group with a positive sigma value as defined by Hammett's Equation". Any electron-donating or electron-withdrawing group may be employed. Examples of electron-donating groups include alkoxy containing 1 to 20 carbon atoms, phenoxy and —NHR' wherein R' is hydrogen, alkyl usually containing 1 to 20 carbon atoms or phenyl. Examples of electron-withdrawing groups include F, Cl, Br, I, $CF_3$, $CH_3SO_2$,

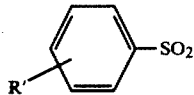

wherein R' has the same meaning given above, $CH_2Cl$, CN, $SO_3$—, $SO_2NR'R''$ wherein R' has the same meaning given above and R" is hydrogen, alkyl usually containing 1 to 20 carbon atoms or phenyl, CONR'R" wherein R' and R" have the same meaning given above, $COOC_2H_5$, $COCH_3$, $NO_2$ and $SO_2CF_3$. Usually, the electron-donating group has a negative sigma value of not more than about 0.90 and the electron-withdrawing group has a positive sigma value of not more than about 1.00.

If desired, the $R^1$ and $R^2$ groups as well as the Z moiety can be used to provide a photographically useful reagent by functionalizing said $R^1$, $R^2$ and Z with the appropriate substituents. In a preferred embodiment, $R^2$ is hydrogen or alkyl.

The moiety selected for Z should undergo β-elimination at a rate such that this and the subsequent reactions provide the 1,3-disulfonylcycloalkane silver solvent at a photographically useful rate, and in a preferred embodiment, the β-elimination of Z provides a photographically useful reagent. β-elimination reactions including those activated by sulfonyl groups are well known, and rate constants for various leaving groups in elimination reactions of β-substituted sulphones have been reported by Charles J. M. Stirling, Acc. Chem. Res. 12, 198 (1979) and Charles J. M. Stirling et al, J. Chem. Soc. Chem. Commun., 941 (1975). In the present invention any of the commonly used leaving groups can be employed as Z, which leaving groups may comprise the appropriate substituents to provide the desired photographically useful reagent upon β-elimination. Typical leaving groups that may be employed as Z include —SMe; —SPh; —$SO_2Me$; —$SO_2Ph$; —SePh; —OPh; —OMe; —P(O)$(OEt)_2$; —NTs; —C$(Me)_2NO_2$; —N(Me)Ts; —N(Me)Ac; —N(Ph)Ac; —N(Ph)Ts; —N(Ph)$CO_2CH_2Ph$; —N(Me)$CO_2Ph$;

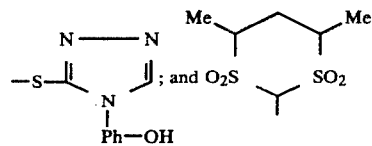

wherein Me; Et, Ph, Ac and Ts represent methyl, ethyl, phenyl, acetyl and tosyl, respectively. It will be appreciated that the above-denoted tetrazole and disulfone moieties would provide a second silver halide solvent.

Following an initial ionization step in aqueous alkali, the silver halide solvent is released from the silver solvent precursor compounds of the present invention by an

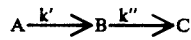

series of reactions wherein the reaction rates k' and k" can readily be determined using standard solution kinetic procedures. The particular A→B→C reaction series of the present invention is illustrated below.

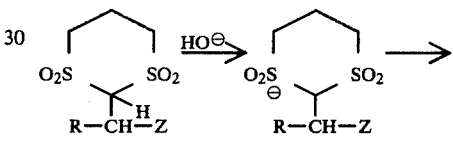

ionization    A

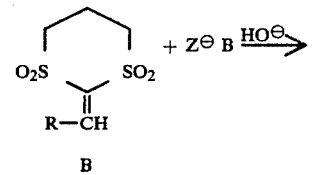

B

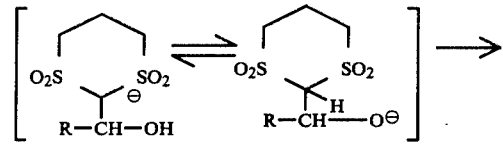

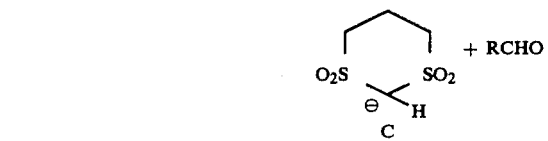

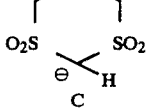

C

The rate of release of silver halide solvent from the subject precursor compounds is alkali dependent, and this rate can be controlled at a given alkali concentration by the selection of the $R^1$ and $R^2$ groups and Z moiety. More particularly, the reaction rate (k') for the formation of B and the reaction rate (k") for the formation of C and their relationship to each other can be varied by appropriate selection of $R^1$ and $R^2$ and Z, and when $R^1$ or $R^2$ is phenyl, these rates can be further adjusted by selection of the appropriate electron-donating or electron-withdrawing substituents. Also, the rate k' relative to k" can be adjusted to give a desired relationship between induction period and the rate of silver halide solvent formation. The particular $R^1$, $R^2$ groups have the same meaning given above and $R^3$ is hydrogen, alkyl or phenyl; said alkyl containing 1 to 20 carbon atoms.

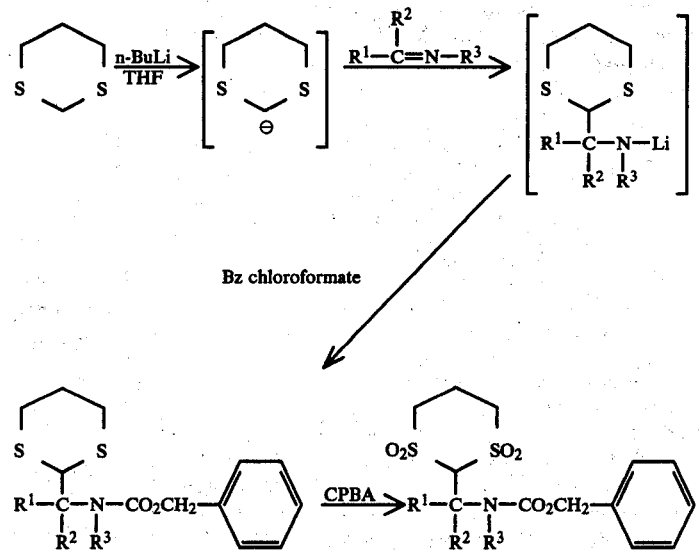

and Z moiety needed to achieve the desired rates at a given pH for a given photographic system may be readily determined empirically.

In comparison to the silver solvent release compounds of aforementioned copending U.S. patent application Ser. No. 294,311, the subject silver solvent precursor compounds involve a series of reactions, i.e., a β-elimination reaction prior to the Michael addition of hydroxide and the retro-aldol reaction. The inclusion of this additional reaction step in the solvent release mechanism provides several advantages, for example, the ability to incorporate an induction period by appropriate selection of

rates and the ability to release a photographically useful reagent via Z in addition to the $R^1$, $R^2$ groups. Als, storage stability is enhanced since water cannot add to the silver halide solvent precursor before the ionization-elimination reaction which does not occur before the application of an alkaline processing composition.

The subject silver solvent precursor compounds may be synthesized in a conventional manner. For example, the 1,3-dithiane or other 1,3-dithio starting material may be reacted with n-butyllithium in tetrahydrofuran at a temperature between about 0° C. and −70° C., usually −30° to −70° C. to generate the dithiane anion followed by reaction also at reduced temperatures with the selected $R^1$—$CR^2$—Z reagent or with a reagent $R^1$—$CR^2$—Z' wherein Z' is a precursor to Z. Where $R^1$—$CR^2$—Z' is employed, the intermediate obtained is reacted further with a reagent or reagents to complete the Z moiety. The 2-substituted 1,3-dithio compound is then converted to the 1,3-disulfone product by oxidation with m-chloroperbenzoic acid (CPBA) or other suitable oxidant at a temperature appropriate to complete the oxidation reaction. The following reaction sequence illustrates the synthesis of one class of silver solvent precursors of the present invention wherein $R^1$—$CR^2$—Z' is $R^1$—$CR^2$=N—$R^3$ wherein $R^1$ and $R^2$ Rather than chloroformates, acid or sulfonyl chlorides, such as, tosyl chloride or acetyl chloride may be employed in the scheme shown above except that it may be desirable to acidify and isolate the lithiated intermediate before reaction with the acid or sulfonyl chloride.

The following examples are given to further illustrate the present invention and are not intended to limit the scope thereof.

EXAMPLE 1

Preparation of the compound having the formula

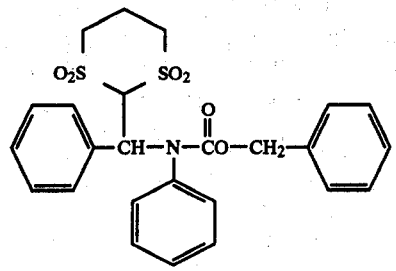

1,3-Dithiane (6.01 g) was dissolved in 250 ml of dry tetrahydrofuran at room temperature, and after cooling to −70° C., 22 ml of 2.4M n-butyllithium in hexane was added dropwise while stirring under nitrogen. The solution was allowed to warm to −15° to −40 ° C. for two hours, and then cooled to −70° C. N-Benzylidene anil (9.06 g) was added portionwise via solid addition through a flextube. Initially solution was complete (yellow), and after coming to room temperature and standing for one hour, buff-white solids precipitated. The reaction mixture was then cooled to −40° C. and 7.5 ml of benzyl chloroformate was added. After addition was complete, the mixture was allowed to come slowly to room temperature. The solids dissolved and the reaction mixture was diluted with one liter of ether. The ether solution was washed with water (2×250 ml), dried over sodium sulfate, filtered and evaporated leaving a tacky amber oil. The oil was dissolved in a small amount of methylene chloride and applied to a column of silica gel (300 g, 100-200 mesh). The column was eluted with methylene chloride and finally with 1% methanol in methylene chloride. 11 grams of the desired material was collected. This material comprised the intermediate having the formula

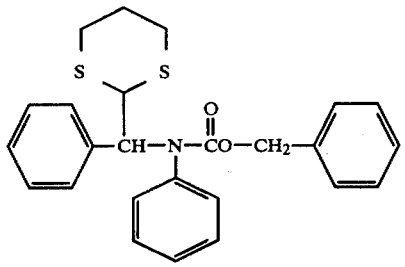

A portion of the material collected (8.71 g) was dissolved in 150 ml of chloroform. The resulting solution was cooled to −30° C. in a dry-ice/acetone bath under nitrogen and 15.9 g of m-chloroperbenzoic acid in 130 ml of chloroform was added dropwise with stirring. The reaction mixture was allowed to come to room temperature slowly and then stirred at room temperature overnight. The reaction mixture was filtered through a Celite pad to remove the white precipitate (m-chlorobenzoic acid) and the pad was washed with chloroform. The chloroform filtrate was washed with 200 ml of 10% sodium sulfite to destroy excess peroxides, then with a pH 7.5 phosphate buffer to remove any dissolved m-chlorobenzoic acid (3×100 ml), and finally with 100 ml of water. After drying over sodium sulfate, the chloroform solution was filtered and the solvent removed by vacuum evaporation to give a white froth. 300 ml of ethanol was added to the froth and stirred at room temperature for one hour. The white solids were collected by filtration, washed with ethanol and air dried. After continued drying under high vacuum at 35°-40° C., 9.4 g of the title compound was obtained as a white solid. The PMR spectrum (DMSO$_{d6}$) was consistent with the assigned structure.

EXAMPLE 2

Preparation of the compound having the formula

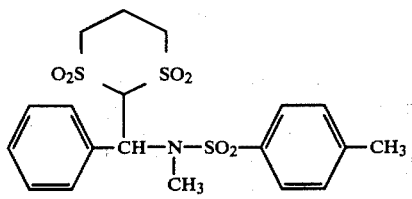

1,3-Dithiane (6.01 g) was dissolved in 200 ml of dry tetrahydrofuran in a nitrogen atmosphere, and after cooling the solution to −70° C., 22 ml of 2.4M n-butyllithium in hexane was added via syringe. The resulting solution was stirred for 30 minutes and 6.2 ml of N-benzylidenemethylamine was added dropwise. After addition, the reaction mixture was allowed to come to room temperature slowly and then a concentrated solution of ammonium chloride in water (0.06 mole) was added. The reaction mixture was extracted with ether and the ether extract was washed with water, dried over sodium sulfate, filtered and the solvent removed by vacuum evaporation to give 10.7 g of a yellow oil comprising the intermediate having the formula

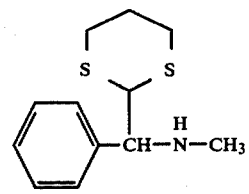

After vacuum drying, 1.64 g of the intermediate, obtained pure from medium pressure chromatography, was dissolved in 25 ml of methylene chloride. 4-Dimethylaminopyridine (860 mg) was added and the reaction mixture cooled in an ice bath. Then 3 g of p-toluenesulfonyl chloride was added portionwise and the reaction mixture was stirred for 96 hours. Another 1.0 g of p-toluenesulfonyl chloride was added, and stirring was continued for several hours. The reaction mixture was poured into ice water, stirred 2 hours, and dilute HCl was added until the mixture was acidic. The methylene chloride layer was separated, washed with water (2×), dried over sodium sulfate, filtered and the solvent removed by vacuum evaporation leaving 4.33 g of an oily residue which contained some unreacted p-toluenesulfonyl chloride. 25 ml of 2N KOH and 10 mls of methanol was added to the residue. This solution was stirred at 40°-45° C. for 3 hours; the methanol was removed by vacuum evaporation; and the residue was extracted with chloroform. The chloroform extract was washed with water, dried over sodium sulfate, filtered and the solvent removed to give 2.42 g of the intermediate, free of p-toluenesulfonyl chloride, having the formula

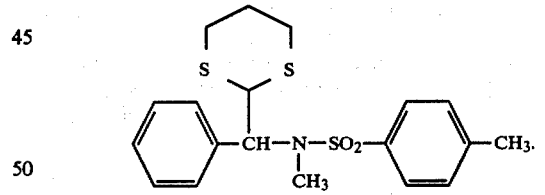

The above intermediate (2.4 g) was added to a solution of 4.75 g of m-chloroperbenzoic acid in 75 mls of chloroform at about −30° C. The reaction mixture was stirred at room temperature under nitrogen for 3 days. The mixture was filtered to remove solids, and the filtrate washed with 20% sodium sulfite until a test with starch-iodide paper was negative then with 10% sodium bicarbonate (3x) and with saturated sodium chloride solution. After drying the chloroform solution over sodium sulfate, it was filtered and the solvent removed leaving an oily residue. Ether was added to the residue and a white solid formed. The solution was filtered giving 80 mg of the title compound. Its PMR spectrum was consistent with the assigned structure.

EXAMPLE 3

Preparation of the compound having the formula

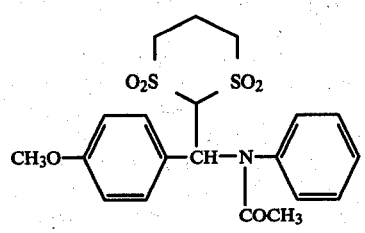

1,3-Dithiane (6.97 g) was dissolved in 290 ml of dry tetrahydrofuran at room temperature and after cooling to −70° C. in a dry ice/hexane bath, 25.4 ml of 2.4M n-butyllithium in hexane was slowly added and the reaction solution was allowed to warm to −30° C. After cooling back to −65° C., 12.5 g of

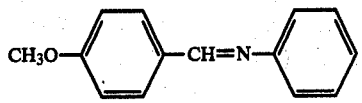

was added portionwise through a "solid addition funnel". After addition was complete, the reaction mixture was removed from the cooling bath and allowed to come to room temperature to insure complete reaction. The cream colored slurry was cooled and dilute hydrochloric acid added until the reaction solution was slightly acidic. The reaction mixture was filtered to remove a small amount of an orange solid, and the filtrate concentrated. The residue was taken up in about one liter of methylene chloride and washed with brine solution. The methylene chloride layer was separated, dried over sodium sulfate, filtered, and the solvent removed under reduced pressure to give 23.2 g of a dark orange-amber viscous oil. The crude product was purified by high pressure chromatography using methylene chloride as the eluent to give 17.6 g of a colorless oil which crystallized on standing. The PMR spectrum in CDCl₃ was consistent with

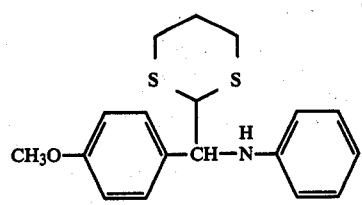

This intermediate (1.15 g) was refluxed with acetyl chloride (0.3 g) in dry benzene for ¼ hour. Another 0.3 g of acetyl chloride was added and reflux continued for 2 hours to drive the acetylation reaction to completion. The solvent and excess acetyl chloride was removed under reduced pressure leaving 1.26 g of a pale straw colored froth. The PMR spectrum in CDCl₃ was consistent with

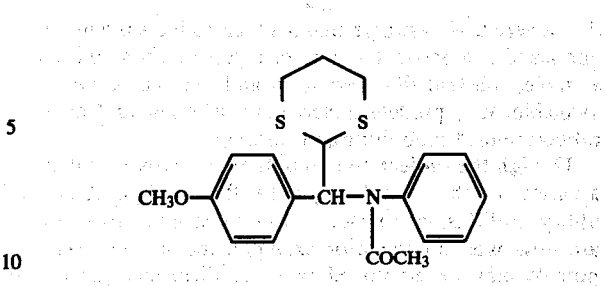

The above intermediate (1.26 g) was dissolved in 30 mls of chloroform and cooled to −20° C. A solution of m-chloroperbenzoic acid (3.20 g, 80-90%) dissolved in 40 mls of chloroform was added over a period of about 15 minutes. The resulting white slurry was stirred under nitrogen overnight while coming to room temperature during this time. The reaction mixture was filtered through Celite, the solids washed with chloroform and the combined filtrates washed successively with 100 mls 10% sodium bisulfite (2x), 100 mls of pH 7.4 phosphate buffer (2x) and finally with 100 mls water. After drying briefly over sodium sulfate, the chloroform solution was filtered through a bed of fresh sodium sulfate and evaporated under reduced pressure to give a white solid that was triturated several times with ether to give 0.99 g of the title compound as a cream colored solid. Its PMR spectrum in CDCl₃ was consistent with the proposed structure.

As noted above, silver halide solvent is released from the silver solvent precursor compounds of the present invention by an

series of reactions wherein k' represents the reaction rate for the β-elimination reaction and k" represents the reaction rate for release of silver halide solvent via the retro-aldol reaction following Michael addition of hydroxide to "B".

FIG. 1 is a graph representative of the A→B→C series reactions of the subject compounds in alkali which is specific to the compound of Example 1. This graph was obtained by mixing a 2×10⁻⁴M solution of the compound of Example 1 in 30% acetonitrile/water with another solution containing 0.5N KOH in 30% acetonitrile/water and then measuring the UV absorbance over a period of 2 seconds at 22° C. The absorbance at a single wavelength was then plotted versus time.

Graphs for the compounds of Examples 2 and 3 were obtained similarly. The rates, k' and k", for each of the compounds of Examples 1, 2 and 3 which were calculated from the graphs are set forth in the following Table.

TABLE

| Ex. No. | k' (sec.⁻¹) | k" (sec.⁻¹) |
| --- | --- | --- |
| 1 | 2.97 | 4.93 |
| 2 | 24.4 | 4.60 |
| 3 | 5.43 | 1.34 |

Figure 2:
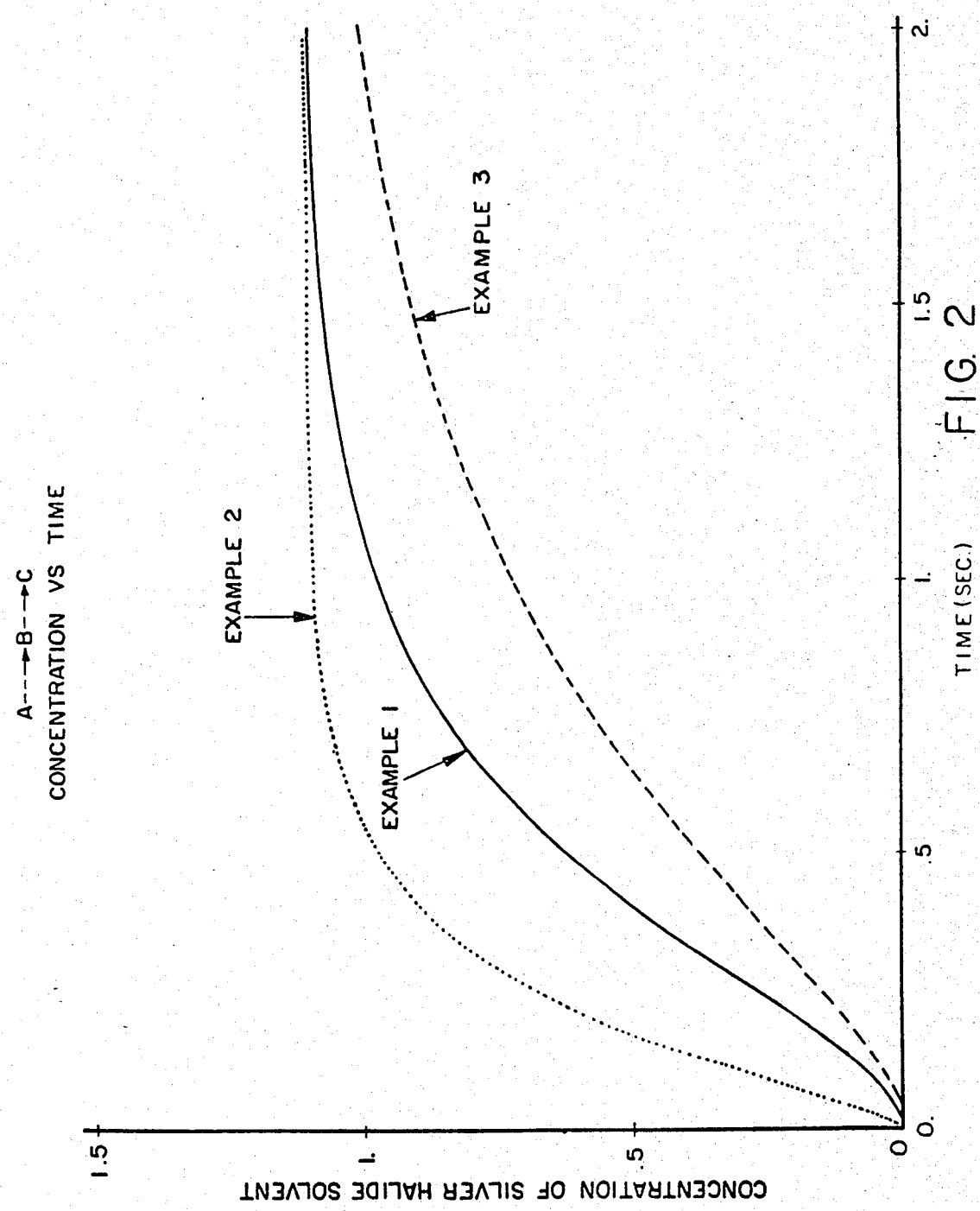
FIG. 2 is a graphic illustration showing concentration of silver halide solvent released as a function of time from three silver solvent release compounds of the present invention (Examples 1, 2 and 3), in alkaline acetonitrile solution.

FIG. 2 is a graph showing the concentration of silver halide solvent released as a function of time for the compounds of Examples 1, 2 and 3.

The subject compounds may be employed in any photographic system for forming images in silver or in dye where it is desirable that a silver halide solvent be contained in a particular layer or layers of a film unit in a stable, substantially inert form and yet can be made available at a predetermined concentration and at a predetermined time during processing.

Though the subject compounds are broadly useful in a variety of photographic systems, they find particular utility in diffusion transfer processes, which processes are now well known. For example, the subject compounds may be employed in silver diffusion transfer processes such as those described in U.S. Pat. No. 2,543,181 issued to Edwin H. Land on Feb. 27, 1951 and U.S. Pat. No. 2,647,056 issued to Edwin H. Land on July 28, 1953 and in numerous other patents.

The compounds of the present invention also may be employed in diffusion transfer processes adapted to provide positive silver transfer images which may be viewed as positive transparencies without being separated from the developed negative silver image including such processes adapted for use in forming additive color projection positive images. Diffusion transfer processes of this type are described, for example, in U.S. Pat. Nos. 3,536,488 and 3,894,871 of Edwin H. Land. The subject compounds also find utility as silver halide solvents in diffusion transfer processes utilizing the properties of the imagewise distribution of silver ions in the soluble silver complex made available in the undeveloped and partially developed areas of a silver halide emulsion to liberate a reagent, e.g., a dye in an imagewise fashion, as described in U.S. Pat. No. 3,719,489 of Ronald F. W. Cieciuch, Roberta R. Luhowy, Frank A. Meneghini and Howard G. Rogers. In addition, it may be desirable to use a silver halide solvent in small amounts in color diffusion transfer processes employing dye developers, such as those disclosed in U.S. Pat. No. 2,983,606.

To illustrate the usefulness of the above-defined compounds in a photographic system, a photosensitive element using as the yellow image dye-providing compound

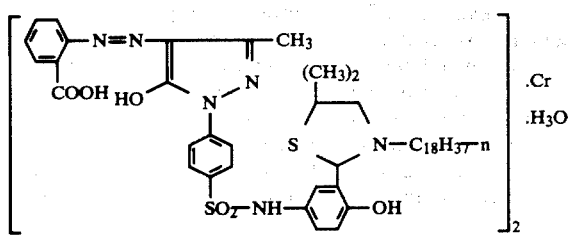

was prepared by coating a transparent polyester film base with the following layers:

1. a layer of said yellow image dye-providing compound dispersed in gelatin and coated at a coverage of 82.5 mgs/ft$^2$ of yellow dye and 41 mgs/ft$^2$ gelatin and including 92.5 mgs/ft$^2$ of the compound of Example 1;
2. a gelatino silver iodobromide emulsion coated at a coverage of 12 mgs/ft$^2$ of silver and 60 mgs/ft$^2$ of gelatin;
3. a layer of gelatin coated at a coverage of 30 mgs/ft$^2$ and containing 2.5 mgs/ft$^2$ of succindialdehyde.

An image-receiving component was prepared by coating a transparent 4 mil polyethylene terephthalate film base with the following layers:

1. as a polymeric acid layer, a mixture of about 9 parts of a partial butyl ester of polyethylene/maleic anhydride copolymer and 1 part of polyvinyl butyral coated at a coverage of about 2,500 mgs/ft$^2$;
2. a timing layer containing a 14:1 ratio of a 60-30-4-6 tetrapolymer of butylacrylate, diacetone acrylamide, styrene and methacrylic acid and polyvinyl alcohol at a coverage of 500 mgs/ft$^2$;
3. a blend of 3 parts by weight of a 2:1 mixture, by weight, of polyvinyl alcohol and poly-4-vinylpyridine and 1 part by weight of a graft copolymer of 4-vinylpyridine and vinylbenzyltrimethylammoniumchloride grafted on hydroxyethyl cellulose in a weight ratio of 2.2/1/2.2, respectively, coated at a coverage of 300 mgs/ft$^2$ to provide an image-receiving layer.

To measure the relative rate of dye transfer as a function of availability of released silver halide solvent, the unexposed photosensitive element was superposed with the image-receiving component. These two components were then taped together with a rupturable container retaining an aqueous alkaline processing composition mounted on the leading edge of these components, so that, upon application of compressive pressure to rupture the container, its contents are distributed between the image-receiving layer and the gelatin overcoat of the photosensitive element. The aqueous alkaline processing composition comprised:

| Processing Composition | |
|---|---|
| Water | 100 cc. |
| Sodium hydroxide | 5 g. |
| Carboxymethyl hydroxyethyl cellulose | 3 g. |
| Titanium dioxide | 50 g. |
| 2-Thiouracil | 0.009 g. |

A layer approximately 0.0020 inch thick of the above-denoted processing composition was distributed between the photosensitive and image-receiving components by passing the superposed components between a pair of pressure-applying rolls. The "sandwich" was maintained intact and the reflection densities were measured as a function of time through the transparent support of the image-receiving component using a densitometer connected to a recorder. The dye transfer densities recorded at 15, 30, 60 and 100 seconds and at about 5 minutes were 0.2, 0.26, 0.32, 0.56 and 1.32, respectively.

Another film unit was prepared in the same manner described above except that the gelatino-silver iodobromide layer contained 30 mgs/ft$^2$ of an oil dispersion of 4'-methylphenylhydroquinone.

This photosensitive element was given an exposure through a stepwedge to white light of 2 mcs, superposed with said image-receiving element, and a layer of said processing composition approximately 0.0020 inch thick was distributed between said elements by passing the film units between a pair of pressure-applying rolls in the dark. The film unit was maintained intact to provide an integral negative-positive reflection print, and kept in the dark at room temperature for 10 minutes. A positive yellow image was visible through the transparent support of the image-receiving component.

As noted above, the subject silver halide solvent precursors are activated to release silver halide solvent by contact with aqueous alkali. Because they are stable, i.e., substantially inert until contacted with the aqueous alkaline processing composition, they may be placed in a variety of locations in the photographic film unit. They may be initially disposed in the photosensitive element, for example, in the silver halide emulsion layer, in a layer of dye image-forming material where appropriate or in a separate processing composition permeable layer, and/or they may be initially disposed in a second sheet-like element, for example, a spreader sheet, an image-receiving element adapted to be superposed with said photosensitive element or an image-receiving component forming part of an integral permanent laminate with said photosensitive element. The particular location selected generally is such that a given amount of silver solvent will be made available at a given position in the photographic system at a given time.

The developing agent, like the silver halide solvent precursor, may be initially included in a layer or layers of the film unit, for example, in the photosensitive element and may be disposed in the same layer as the silver halide solvent precursor. The developing agent also may be initially present in the processing composition, but it will be appreciated that positioning both the developing agent and silver halide solvent precursor in the film unit permits processing of the exposed film unit to be effected simply by applying aqueous alkali. The developing agent, like the silver halide solvent, may be provided as a developing agent precursor which precursor releases the developing agent when contacted with the processing composition. Such compounds are disclosed and claimed, for example, in aforementioned U.S. Pat. No. 3,698,898. Examples of other developing agents that may be employed are the p-aminophenols, the reductones and the various hydroquinones commonly used in the art.

It will be appreciated that the subject silver halide solvent precursors also may be used in admixture with each other and/or in admixture with other silver halide solvents or solvent precursors. When other solvents are used, they may be disposed in the processing composition.

Also, it will be appreciated that the subject compounds may be employed with alkali and viscosity-increasing reagents other than those specified above. For example, the alkali employed may be potassium or lithium hydroxide, and the viscosity-increasing reagent may be a cellulosic polymer, e.g., sodium carboxymethyl cellulose or hydroxyethyl cellulose; an oxime polymer, e.g., polydiacetone acrylamide oxime; or other alkali-stable high molecular weight polymer. Such materials are well known in the art, and indeed, the subject compounds may be used in conjunction with antifoggants, development restrainers, toners, and other components are commonly used in photographic processes.

As mentioned previously, the subject compounds also may be employed in any of the various photographic film units known in the art either for use in conventional, i.e., "tray" photography or for use in diffusion transfer photography, either silver or color, diffusion transfer photography including integral negative-positive film units for preparing color transfer images viewable without separation as reflection prints as described, for example, in U.S. Pat. Nos. 3,415,644 and 3,594,165.

Since certain changes may be made in the herein-defined subject matter without departing from the scope of the invention herein involved, it is intended that all matter contained in the above description should be interpreted as illustrative and not in a limiting sense.

What is claimed is:

1. A compound of the formula

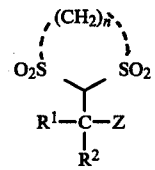

wherein $R^1$ is a monovalent organic radical selected from alkyl, cycloalkyl, alkaryl, aralkyl and heterocyclic aryl; $R^2$ is hydrogen or a monovalent organic radical selected from alkyl, cycloalkyl, alkaryl, aralkyl and heterocyclic aryl; Z is a moiety selected from

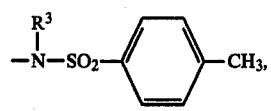

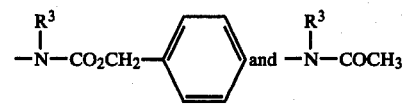

wherein $R^3$ is hydrogen, alkyl or phenyl; and n is an integer 3, 4 or 5.

2. A compound as defined in claim 1 wherein n is 3.

3. A compound as defined in claim 2 wherein $R^2$ is hydrogen.

4. A compound as defined in claim 3 wherein $R^1$ is aryl and Z is

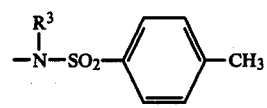

wherein $R^3$ is hydrogen, alkyl or phenyl.

5. A compound as defined in claim 3 wherein $R^1$ is aryl and Z is

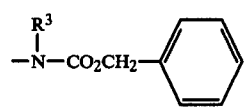

wherein $R^3$ is hydrogen, alkyl or phenyl.

6. A compound as defined in claim 3 wherein $R^1$ is aryl and Z is

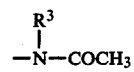

wherein $R^3$ is hydrogen, alkyl or phenyl.

* * * * *